United States Patent [19]

Buultjens et al.

[11] Patent Number: 5,091,173
[45] Date of Patent: Feb. 25, 1992

[54] HAIR GROWTH COMPOSITION

[75] Inventors: Travis E. J. Buultjens; Stephen W. Hellens, both of Dundee; Colin A. B. Jahoda; Roy F. Oliver, both of Fife; Anne P. Withers, Dundee, all of Scotland

[73] Assignee: The University of Dundee, Dundee, Scotland

[21] Appl. No.: 525,171

[22] Filed: May 22, 1990

Related U.S. Application Data

[63] Continuation-in-part of Ser. No. 373,727, Jun. 29, 1989, abandoned.

[51] Int. Cl.$^5$ .............................................. A61K 7/06
[52] U.S. Cl. ...................................... 424/70; 424/115; 424/116; 514/21; 514/880; 530/350; 435/70.2
[58] Field of Search ................... 514/880, 21; 424/70, 424/85.1; 530/350, 351; 435/70.2, 240.2

[56] References Cited

U.S. PATENT DOCUMENTS

| | | | |
|---|---|---|---|
| 4,016,036 | 4/1977 | Green et al. | 424/85.1 |
| 4,139,619 | 2/1979 | Chidsey, III | 424/45 |
| 4,670,255 | 6/1987 | Yoshizumi et al. | 424/93 |
| 4,823,946 | 5/1989 | Green | 424/70 |

FOREIGN PATENT DOCUMENTS

| | | |
|---|---|---|
| 693898 | 2/1967 | Belgium . |
| 221208 | 5/1987 | European Pat. Off. . |
| 225639 | 6/1987 | European Pat. Off. . |
| 335554 | 10/1989 | European Pat. Off. . |
| 0352984 | 1/1990 | European Pat. Off. . |
| 3431266 | 3/1986 | Fed. Rep. of Germany . |
| 2395756 | 6/1977 | France . |
| 2472385 | 7/1981 | France . |
| 61-5006 | 10/1986 | Japan . |
| 63-284112A | 5/1987 | Japan . |
| 7705186 | 5/1977 | Netherlands . |
| 1563824 | 4/1980 | United Kingdom . |
| 2088210 | 6/1982 | United Kingdom . |
| 87/00201 | 1/1987 | World Int. Prop. O. . |

OTHER PUBLICATIONS

Sporn, M. B. and A. B. Roberts, (1988) "Peptide Growth Factors are Multifunctional", Nature, vol. 332, pp. 217-219.

Horne, K. A. et al., (1986) "Hair-Growth-Promoting Properties of Dermal Papilla Cells in the Rat." Journal of Physiology (Lond), p. 48P.

Horne, K. A. et al., (1986) "Whisker Growth Induced by Implantation of Cultured Vibrissa Dermal Papilla Cells in the Adult Rat", Journal of Embryology and Experimental Morphology, vol. 97, pp. 111-124.

Withers, A. P. et al., (1986) "Culture of Wool Follicle Dermal Papilla Cells from Two Breeds of Sheep", Archives of Dermatological Research, vol. 279, pp. 140-142.

Jahoda C. A. B. et al., (1984), "Vibrissa Dermal Papilla Cell Aggregative Behavior in vivo and in vitro", Journal of Embryology and Experimental Morphology, vol. 79, pp. 211-224.

Jahoda, C. A. B. et al., (1984) "Induction of Hair Growth by Implantation of Cultured Dermal Papilla Cells", Nature, vol. 311, pp. 560-562.

Messenger, A. G., (1984) "The Culture of Dermal Papilla Cells from Human Hair Follicles", British Journal of Dermatology, vol. 110, pp. 685-689.

Jahoda, C. A. B. et al., (1984) "Changes in Hair Growth Characteristics Following the Wounding of Vibrissa Follicles in the Hooded Rat", Journal of Embryology and Experimental Morphology, vol. 83, pp. 81-93.

(List continued on next page.)

Primary Examiner—Jose G. Dees
Assistant Examiner—Deborah D. Carr
Attorney, Agent, or Firm—Brahm J. Corstanje; Milton B. Graff, IV; Jerry J. Yetter

[57] ABSTRACT

A composition suitable for topical application to mammalian skin or hair comprising an amount of a cell-free supernatant from a culture of dermal papilla cells sufficient to increase hair growth in mammals.

12 Claims, 2 Drawing Sheets

OTHER PUBLICATIONS

Jahoda, C. et al., (1981) "The Growth of Vibrissa Dermal Papilla Cells in vitro", British Journal of Dermatology, vol. 105, pp. 623-627.

Ibrahim, L. et al., (1977) "Inductive Capacity of Irradiated Dermal Papillae", Nature, vol. 265, pp. 733-734.

Oliver, R. F., (1970) "The Induction of Hair Follicle Formation in the Adult Hooded Rat by Vibrissa Dermal Papillae", Journal of Embryology and Experimental Morphology, vol. 23, pp. 219-236.

Oliver, R. F., (1967) "The Experimental Induction of Whisker Growth in the Hooded Rat by Implantation of Dermal Papillae", Journal of Embryology and Experimental Morphology, vol. 18, pp. 43-51.

Oliver, R. F., (1966) "Whisker Gropwth After Removal of the Dermal Papilla and Lengths of Follicle in the Hooded Rat", Journal of Embryology and Experimental Morphology, vol. 15, pp. 331-347.

Oliver, R. F., (1966) "Histological Studies of Whisker Regeneration in the Hooded Rat", Journal of Embryology and Experimental Morphology, vol. 16, pp. 231-244.

Cohen, J., (1961) "The Transplantation of Individual Rat and Guinea-pig Whisker Papillae", Journal of Embryology and Experimental Morphology, vol. 9, pp. 117-127.

Fig. 1

HAIR GROWTH COMPOSITION

This is a continuation-in-part of application Ser. No. 373,727, filed on June 29, 1989 now abandoned.

BACKGROUND OF THE INVENTION

Mammalian hairs are formed by the differentiation and keratinization of cells produced in the epidermal matrix which invests the dermal papilla at the base of the hair follicle. The importance of the dermal papilla, a discrete population of specialized fibroblasts, in stimulating and controlling the growth of hair has been established in a series of experimental studies using the rat vibrissa follicle, a system first employed by Cohen, J., (1961), J. Embryol. exp. Morph., 9, 117–127. Oliver, R. F., (1966), J. Embryol. exp. Morph., 15, 331–347 and Oliver, R. F., (1966), J. Embryol. exp. Morph., 16, 231–244, demonstrated that following removal of the dermal papilla, hair growth ceases and it is not resumed until a new dermal papilla regenerates from dermal sheath cells. Transplantation studies have shown that dermal papillae can induce hair growth when implanted into vibrissa follicles (Oliver, R. F., 1967, J. Embryol. exp. Morph. 18, 43–51; and Ibrahim, L. and E. Wright, 1977, Nature, Lond. 265, 733–734) and can interact with ear and scrotal sac epidermis to induce the formation of new follicles and the subsequent growth of hair fibers (Oliver, R. F., 1970, J. Embryol. exp. Morph., 23, 219–236). Wounding of the dermal papilla can lead to production of longer hairs associated with extended growth cycles (Jahoda, C. A. B. and R. F. Oliver, 1984, J. Embryol. exp. Morph., 79, 211–224; and Jahoda, C. A. B. and R. F. Oliver, 1984, J. Embryol, esp. Morph., 83, 81–93).

Microsurgical removal of the vibrissa follicle dermal papilla has allowed the growth of this discrete population of cells in culture (Jahoda, C. A. B and R. F. Oliver, 1981, Br. J. Dermatol., 105, 623–627. When compared with skin fibroblasts, cultured dermal papilla cells display unique morphological and behavioral characteristics and, in particular, form discrete cell aggregates when they approach confluence (Jahoda, C. A. B. & R. F. Oliver, 1984, J. Embryol. exp. Morph., 79, 211–224). Cultured papilla cells of early passage numbers have also been shown to retain the ability to induce the development of new, hair producing bulbs when implanted as pellets into the bases of amputated follicles (Jahoda, C. A. B., K. A. Horne & R. F. Oliver, 1984, Nature, Lond., 311, 560–562; and Horne, K. A., C. A. B. Jahoda & R. F. Oliver, 1986, J. Embryol. exp. Morph., 97, 111–124. These experiments clearly demonstrate the importance of the dermal papilla in the induction and maintenance of hair growth. Two broad classes of interactions can be envisaged involving the dermal papilla and surrounding follicular tissue namely: (1) direct intercellular interactions involving cell contact and (2) bi-directional interactions mediated by diffusible factors. An important class of diffusible effector molecules are the so-called polypeptide growth factors (e.g., hair growth promoters) that can be detected in vitro by their ability to modulate DNA synthesis in appropriate target cells (Sporn, M. B. and A. B. Roberts, 1988, Nature, Lond., 332, 217–219).

SUMMARY OF THE INVENTION

A composition suitable for topical application to mammalian skin or hair, comprising an amount of the cell-free supernatant from a culture of dermal papilla cells which is sufficient to increase hair growth in mammals.

DETAILED DESCRIPTION OF THE INVENTION

As used herein, "conditioned medium" means medium in which cells have been growing for a period of time and are subsequently removed from the medium thereby leaving behind in the medium anything excreted by the cells during their growth.

As used herein, "hair growth promoter" means a compound or composition which induces the formation of a greater number of hair strands, and/or increases the diameter of the hair strand, and/or lengthens the hair strand, and/or prevents, retards, or arrests the process of hair loss.

As used herein, "IGF-I" refers to Insulin-Like Growth Factor-I which is a basic, 7649-molecular weight, 70-amino acid, growth hormone-dependent, single chain peptide. The peptide demonstrates stimulation of sulfate incorporation into cartilage, insulin-like activity in muscle and adipose tissue, and mitogenic activity, particularly in fibroblasts (see Rothe, M. & V. Falanga, "Growth Factors", (1989) Archives of Dermatology 125, 1390–1398.

As used herein, "IGF-II" refers to Insulin-Like Growth Factor II which is a neutral, 7649 molecular weight, 67 amino acid, single chain peptide structurally similar to IGF-I, but much less growth hormone-dependent. IGF-II also demonstrates stimulation of sulfate incorporation into cartilage, insulin-like activity in muscle and adipose tissue, and mitogenic activity, particularly in fibroblasts.

As used herein, "IGF Family" means Insulin-Like Growth Factor Family which includes insulin, IGF-I, and IGF-II.

As used herein, "transformed cell line" means a cell line having two or more of the following properties: 1) the ability to grow in low or no serum, 2) a change from normal chromosome number (aneuploidy), 3) a loss of contact growth inhibition, i.e., the number of cells is no longer limited by the area of the growth dish and the cells will form multilayers; the ability to grow on soft agar is also an example of a loss of contact growth inhibition.

As used herein, a "spontaneously transformed cell line" means a previously normal cell line that has become a transformed cell line in the absence of any added reagent (e.g., mutagen).

As used herein, all percentages are by weight unless otherwise specified.

The composition according to the invention comprises a cell-free supernatant obtained from the culture of dermal papilla cells (conditioned medium) in an amount which is sufficient to increase hair growth in mammals (humans, rats, etc.), when applied thereto, usually topically. Hair growth is increased by at least 10% more than that obtainable using a control composition from which said cell-free supernatant has been omitted.

The cell-free supernatant (conditioned medium) useful in compositions of the present invention is preferably obtained from the culture of transformed dermal papilla cells. The transformed dermal papilla cells differ from primary dermal papilla cells obtained from hair follicles in that the transformed cells can be serially transferred indefinitely (greater than about 50 passages) whereas primary dermal papilla cell cultures obtained from hair follicles undergo terminal senescence after about 10–15 passages. A preferred transformed dermal papilla cell line for obtaining the cultures useful in the present invention is the DP-B cell line disclosed hereinafter.

Preferably, the cell-free culture supernatant is concentrated, for example by ultra filtration, at least about 40 or 50 times, most preferably at least 100 times.

The procedure for culture of dermal papilla cells (fibroblasts) and isolation of the culture supernatant and its concentration is described more fully later in this specification.

The cell-free supernatant has been shown to contain a proteinaceous hair growth promoter. The cell-free supernatant is further characterized in that it preferably comprises about 5 ng/ml to about 200 ng/ml of one or more members of the IGF Family selected from the group consisting of insulin, IGF-I, and IGF-II, preferably IGF-I; more preferably from about 7 ng/ml to about 22 ng/ml.

The composition according to the invention more particularly comprises a proteinaceous hair growth promoter which is further characterized by:

(a) preferably having a molecular weight of at least 500D; and (b) possessing the ability to initiate DNA synthesis in a culture of serum-starved NIH 3T3 cells (e.g., NIH 3T3 cell line or Balb/c 3T3 cell line), that is, resting cells maintained in a nutrient medium containing 0.2% to 0.5% by volume of serum.

DNA synthesis can be determined by measuring the uptake of tritiated thymidine by the method as hereinafter described.

The hair growth promoter can be obtained by culturing dermal papilla cells in nutrient medium followed by separation of the supernatant liquid from such cultures, centrifuging the supernatant to retain cells and cell debris, and concentrating and filtering the supernatant to remove substances having an apparent molecular weight of greater than about 500D, preferably greater than about 5000D.

The cell free concentrate so obtained contains the hair growth promoter having an apparent molecular weight of at least 500D, preferably from 500D to 1,000,000D, more preferably at least about 5000D, more preferably still from about 5000D to about 15000D, which is then incorporated in a composition according to the invention together with a suitable vehicle. Alternatively, the cell free concentrate after dialysis can be dried, preferably by freeze drying, prior to incorporation in a composition according to the invention.

Although the hair growth promoter generally has an apparent molecular weight of greater than 500D, it is believed that certain fragments derived from the hair growth promoter can also show activity in promoting hair growth or regrowth.

The amount of this hair growth promoter to be incorporated with a suitable vehicle into compositions for topical use can vary widely, but in general, an amount expressed as protein of from about 0.00001% to about 99%, preferably from about 0.001% to about 90%, more preferably from about 0.5% to about 50%, more preferably still from about 1% to about 10% by weight of the composition will provide an adequate dose of the hair growth promoter to the skin following topical application.

The Vehicle

The composition according to the invention also comprises a solid, semi-solid or liquid cosmetically and/or physiologically acceptable vehicle, to enable the hair growth factor substance to be conveyed to the skin at an appropriate dilution. The nature of the vehicle will depend upon the method chosen for topical administration of the composition. The vehicle can itself be inert or it can possess physiological or pharmaceutical benefits of its own.

The selection of a vehicle for this purpose presents a wide range of possibilities depending on the required product form of the composition. Suitable vehicles can be classified as described hereinafter.

It should be explained that vehicles are substances which can act as diluents, dispersants, or solvents for the hair growth promoter which therefore ensure that it can be applied to and distributed evenly over the hair and/or scalp at an appropriate concentration. The vehicle is preferably one which can aid penetration of the hair growth promoter into the skin to reach the immediate environment of the hair follicle. Compositions according to this invention can include water as a vehicle, and/or at least one cosmetically acceptable vehicle other than water, including the concentrated dialyzed culture supernatant, which will normally be aqueous in nature, obtained by the concentration step referred to earlier in this specification.

Vehicles other than water that can be used in compositions according to the invention can include solids or liquids such as emollients, solvents, humectants, thickeners and powders. Examples of each of these types of vehicles, which can be used singly or as mixtures of one or more vehicles, are as follows:

Emollients, such as stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate;

Propellants, such as trichlorofluoromethane, dichlorodifluoromethane, dichlorotetrafluoroethane, monochlorodifluoromethane, trichlorotrifluoroethane, propane, butane, isobutane, dimethyl ether, carbon dioxide, nitrous oxide;

Solvents, such as ethyl alcohol, methylene chloride, isopropanol, castor oil, ethylene glycol monoethyl ether, diethylene glycol monobutyl ether, diethylene glycol monoethyl ether, dimethyl sulphoxide, dimethyl formamide, tetrahydrofuran;

Humectants, such as glycerin, sorbitol, sodium 2-pyrrolidone-5-carboxylate, soluble collagen, dibutyl phthalate, gelatin;

Powders, such as chalk, talc, fullers earth, kaolin, starch, gums, colloidal silicon dioxide, sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The amount of vehicle in the composition, including water if present, should preferably be sufficient to carry at least a portion of a selected hair growth factor substance to the skin in an amount which is sufficient to effectively enhance hair growth. The amount of the vehicle can comprise the balance of the composition, particularly where little or no other ingredients are present in the composition. Accordingly, the vehicle or vehicles can comprise from about 1 to about 99.9999%, more preferably from about 10% to about 99.999%, more preferably still from about 50 to about 95.5% and most preferably from about 90 to about 99% by weight of the composition.

EXAMPLE

Cell Culture

The rat vibrissa dermal papilla cell line, DP-B, a transformed dermal papilla cell line, was obtained as a frozen cell stock. The cells used in $^3$H-thymidine incorporation assays were as follows: primary adult rat vibrissa and human hair follicle dermal papilla cells which were established as previously described (Jahoda, C. A. B. & Oliver, R. F. (1981), Br. J. Dermatol., 105, 623–627; Jahoda, C. A. B. & Oliver, R. F. (1984, J. Embryol. exp. Morph, 79, 211–224); primary rat and human skin fibroblasts were established by dissection and explantation and the Balb/c 3T3 cell line (obtained from Beaston Institute, Glasgow, U.K.). All media and media supplements were obtained from Gibco, U.K.

Growth Studies a) Serum dependence

DP-B and primary rat dermal papilla cells were seeded at $10^4$ cells per well in 24-well multidishes (Nunc) and maintained for 24 hours in Eagle's Minimal Essential Medium (EMEM), supplemented with 10% fetal calf serum (FCS), 4 mM glutamine and 50 U/ml penicillin/streptomycin at 37° C. in 5% $CO_2$. This medium was removed and the cells washed extensively with Hank's Balanced Salt Solution (HBSS) before fresh EMEM 10% FCS or EMEM containing only 1% FCS was added to the cells (Day O). At each time point duplicate samples of cells were removed from the wells by trypsinisation and centrifuged at 200×g for 5 minutes before being resuspended in 5 ml of filtered 0.9% (w/v) saline for counting (Coulter Counter).

b) Response of Balb/c 3T3 Cells to DP-B Conditioned Medium

Balb/c 3T3 cells were grown for three successive passages in Dulbecco's Modified Eagle's Medium supplemented with 1% FCS and 50 U/ml penicillin/streptomycin (DMEM 1% FCS), plated out at $10^4$ cells/well of 24-well multidishes and maintained in DMEM 1% FCS at 37° C. in 5% $CO_2$. After 24 hours (Day O) the cells were washed extensively in HBSS and replicate cultures were treated on Days O, 2 and 4 with 1.0 ml of one of the following treatments:

(i) DMEM 10% FCS, (ii) serum-free DMEM, (iii) 20-fold concentrate of DP-B conditioned medium and (iv) DP-B conditioned medium. At each time point replicate cultures were tryprinized and cell numbers were assessed as described above.

Preparation of DP-B Conditioned Media

DP-B cells were grown in EMEM supplemented with 10% FCS, 4 mM glutamine and 50 U/ml penicillin/streptomycin at 37° C. with 5% $CO_2$ in 150 cm plastic tissue flasks (Sterilin) or 100×270 mm Borosilicate Roller Bottles (New Brunswick Scientific) until sub-confluent. The growth medium was then removed, the cells were washed extensively with PBS and maintained in serum-free Dulbecco's Modified eagle's Medium (DMEM) for 48–72 hours at 37° C. in 5% $CO_2$. The medium was then removed, centrifuged at 14,500×g for 1 hour followed by 100,000×g for 16 hours, resterilized with a 0.22 μm Millex EV filter Unit (Millipore) and stored at $-70°$ C.

$^3$H[methyl] Thymidine Incorporation Assay

Balb/c 3T3 cells were seeded at $2.5\times 10^4$ per well in 24-well multidishes for 24–48 hours in DMEM supplemented with 10% FCS and 50 μ/ml penicillin/streptomycin at 37° C. in 5% $CO_2$. The medium was removed, the cells were washed twice with PBS and then starved overnight with 1.0 ml of DMEM supplemented with 0.2% FCS. 0.5 ml of the medium was removed and conditioned media samples or serum-free DMEM controls were added to a final volume of 1.5 ml. The assay plates were incubated for approximately 8 hours at 37° C. in 5% $CO_2$ before H[methyl] thymidine (2μCi/ml) was added. The plates were incubated for 18 hours, the thymidine-containing media removed, cells washed with HBSS and fixed at room temperature with 50% methanol in HBSS (15 minutes) followed by ethanol (15 minutes). The cells were treated with 10% trichloroacetic (TCA) acid for two 15 minute periods at 4° C., washed with 3:1 methanol/ether and air dried. The fixed cells were lysed overnight with 1.0 ml 0.2 N sodium hydroxide at 4° C., the lysates were acidified with 100 μl glacial acetic acid and counted in 20 ml "Ecoscint" scintillation fluid (National Diagnostics).

When cells other than Balb/c 3T3 were used as targets for thymidine incorporation they were grown and maintained at confluence for 3 days in 1 ml complete medium before addition of test and control samples as described above.

Ultrafiltration of DP-B Conditioned Medium

DP-B conditioned media (250 ml) were prepared using Borosilicate Roller Bottle cultures as previously described. The media and additive-free DMEM control media were concentrated 40-fold using an Amicon Thin Channel Ultrafiltration System containing an Amicon YM5 low protein binding membrane (MW cut-off 5 K).

The concentrates were resterilized with 0.4 μm Millex AA and 0.22 μm Millex GV filter unites (Millipore), serially diluted with additive-free DMEM and tested with the ultrafiltrate in the Balb/c 3T3 Thymidine Incorporation Assay described above.

Protease Treatment

Test samples of DP-B conditioned medium were treated with a mix of trypsin Type III (Sigma 10000 U/mg) and α-chymotrypsin Type I-S (Sigma 60 U/mg) each of 100 μg/ml. Control samples of DP-B conditioned medium were incubated with either (i) Dulbecco's MEM or (ii) a heat inactivated (20 minutes at 100° C.) mix of trypsin and α-chymotrypsin at the above concentrations. All incubations were carried out for 4 hours at 37° C. after which each sample received 1 mg/ml of soybean trypsin inhibitor Type I-S (Sigma). Test and control samples were assayed on Balb/c 3T3 cells as described above.

Preparation of Conditioned Medium from Cycloheximide-Treated Cell Cultures

Subconfluent 150 cm$^2$ cultures of DP-B cells were washed extensively with HBSS and treated with serum-free DMEM containing 20 μg/ml of cycloheximide (Calbiochem) for 48 hours. The conditioned medium was then collected, centrifuged and received three consecutive treatments on PD10 (Sephadex G25) gel filtration columns (Pharmacia) equilibrated with 20 mM MaCl. The gel filtration procedure was introduced in order to remove cycloheximide (M.W. 281.35) from the conditioned medium. Void volume fractions (3 ml) were collected after each consecutive treatment and the stimulatory activity in the last fraction was assayed on Balb/c 3T3 cells as described above. The efficiency of removal of cycloheximide by the PD10 desalting column was confirmed by comparing the stimulation over control levels of $^3$H-thymidine incorporation into Balb/c 3T3 cells following treatment with normal conditioned medium and that given by conditioned medium to which 10 μg/ml cycloheximide was added just prior to the gel filtration procedure described above.

Growth Studies

Figure 1:
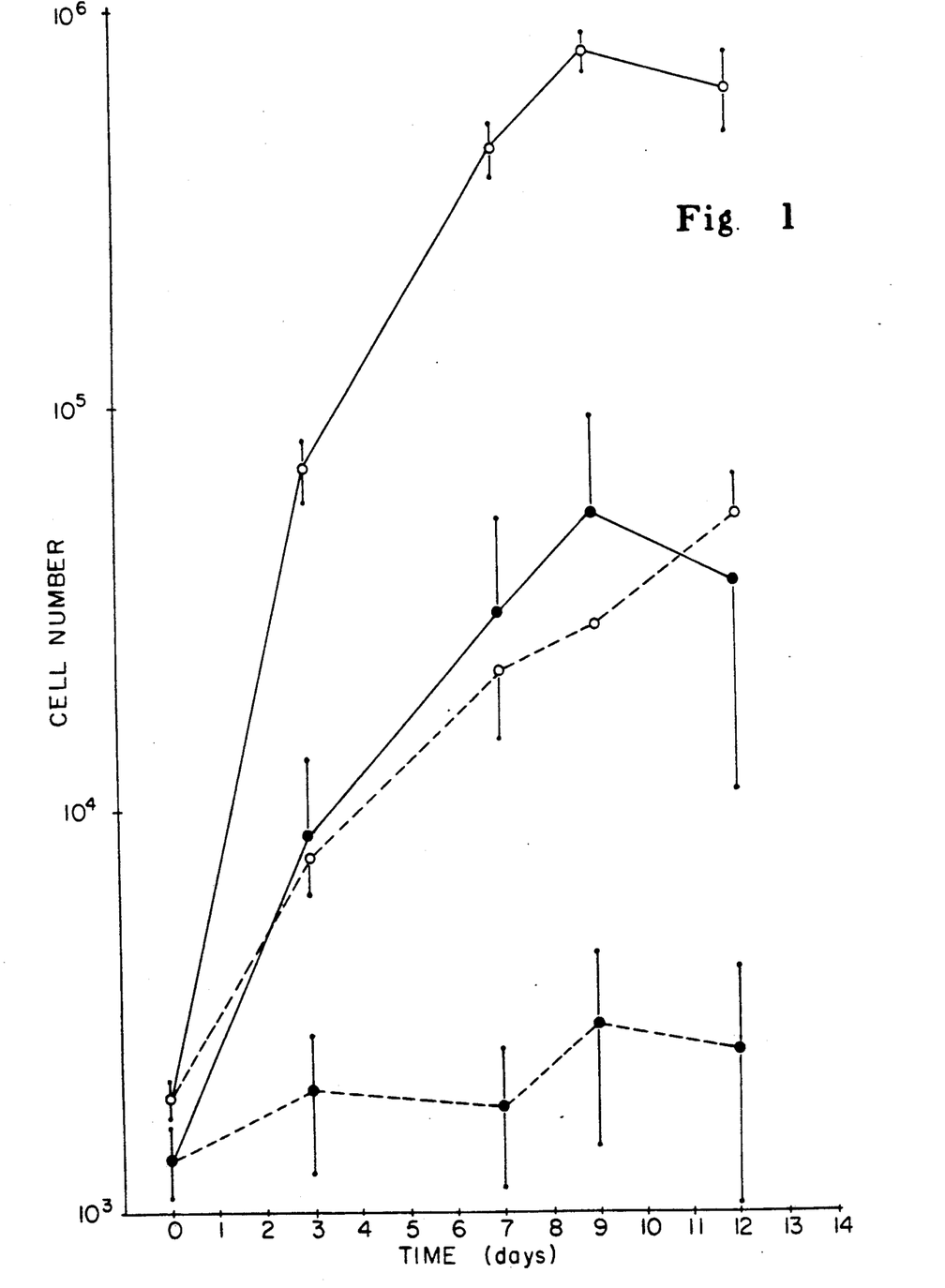
FIG. 1 illustrates growth curves of the DP-B cell line and primary rat vibrissa dermal papilla cell. The growth curves were obtained as described in the example below for DP-B cells (o) and primary dermal papilla cells ( ) in EMEM supplemented with 1% (pecked line) and 10% (solid line) fetal calf serum. Each point represents the mean value from replicate cultures and the bars indicate the standard error.

Typical growth curves for the DP-B cell line and a primary rat dermal papilla cell culture grown in EMEM supplemented with 1% FCS and 10% FCS are shown in FIG. 1. The first sample count taken at Day O shows that the plating efficiency of the two cell types at this stage were similar and therefore the subsequent observed differences in growth were not due to variations in cell attachment. The DP-B cells grown in medium containing 10% FCS, immediately enter a very rapid phase of proliferation and for the first 72 hours of growth their population doubling time is considerably shorter than that of the primary dermal papilla culture in the same medium (Table 1). DP-B cells grown in medium containing 1% FCS, do not grow as rapidly as they do in 10% FCS, but, unlike the primary culture, they do proliferate throughout the time course of this experiment (Table 1). DP-B cells also attain a much higher saturation density than the primary dermal papilla cells.

H[methyl] Thymidine Incorporation Assays

Figure 2:
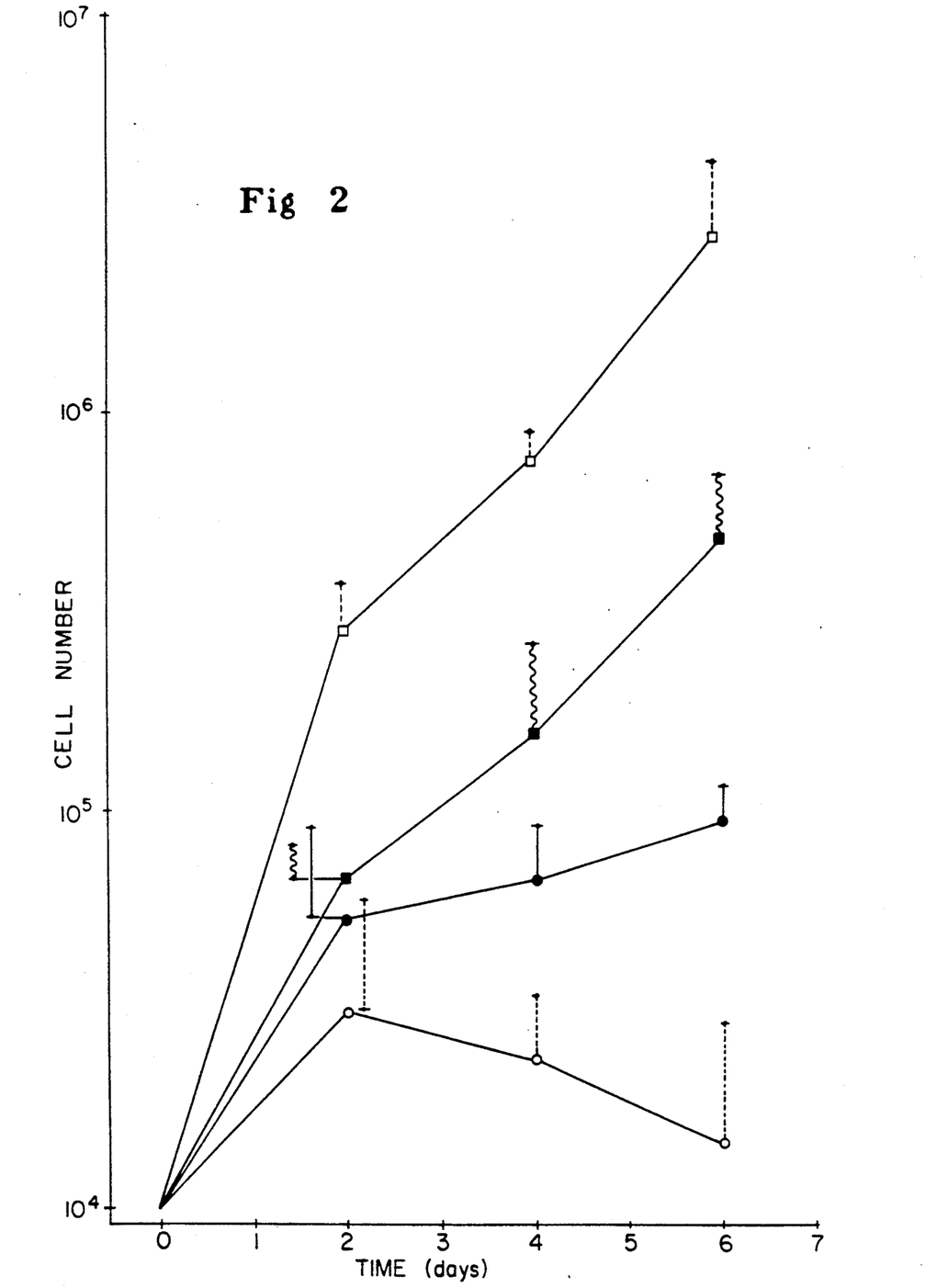
FIG. 2 illustrates growth response of Balb/c 3T3 cells to DP-B conditioned medium. The growth curves were obtained as described in the example below for Balb/c 3T3 cells in serum-free DMEM (o), normal (lx) DP-B conditioned medium (●), 20-fold concentrate of DP-B conditioned medium (■) and DMEM supplemented with 10% fetal calf serum (□). Each point represents the mean value from triplicate cultures and the bars indicate the standard error.

The effect of DP-B conditioned medium on $^3$H[methyl]thymidine incorporation into a range of quiescent target cells is shown in FIG. 2. The DP-B conditioned medium can stimulate a 2 to 3-fold increase in incorporation of labelled thymidine into the DNA of all of the target cells tested.

Concentration-Dependent Response of Balb/c 3T3 Cells to DP-B Conditioned Medium A 20-fold concentration of DP-B conditioned medium was obtained by membrane ultrafiltration (membrane retention limit approximately 5 KD). Serial doubling-dilutions (up to 2.5-fold) of the concentrate, the 20-fold concentrate and a dilution of the 20-fold concentrate which was equivalent to the starting material (designated as 1x) were assayed on Balb/c 3T3 cells. The data show that the stimulation of incorporation of $^3$H-thymidine into TCA-precipitate material is directly related to the degree of concentration of the conditioned medium (Table 3). This was not observed when the retentate obtained by ultrafiltration of additive-free DMEM (control medium) was diluted as above and tested on Balb/c 3T3 cells (Table 3). In both cases the ultrafiltrate showed no significant effects on the DNA synthesis of Balb/c 3T3 cells.

The effects of a 20-fold concentrate of DP-B conditioned medium on the proliferation of Balb/c 3T3 cells is shown in FIG. 2. The data show that DP-B conditioned medium (1) contains mitogenic activity that maintains cell proliferation at rates that are intermediate between that of serum-free DMEM and DMEM supplemented with 10% serum and (2) that this mitogenic activity is enhanced in samples concentrated by membrane ultrafiltration.

The activities in DP-B conditioned medium that stimulate cell proliferation and DNA synthesis could not be concentrated on a Minicon B15 membrane filtration unit (retention limit approximately 15 KD).

Effects of Cycloheximidine and Protease Treatment on DP-B Conditioned Medium Membrane ultrafiltration studies indicates that the stimulatory activity of DP-B conditioned medium is in the molecular weight range 5-15 KD. When conditioned medium is pre-incubated with a mix of trypsin and chymotrypsin at 80-90% inhibition of $^3$H-thymidine incorporation with respect to either untreated condition medium or conditioned medium treated with heat-inactivated proteases is observed on the Balb/c assay (data not shown). This evidence of the polypeptide or protein-nature of the stimulatory activities in conditioned medium is confirmed by cycloheximide treatment of DP-B cells. Conditioned medium prepared from cycloheximide-treated DP-B cells was assayed for a reduction in stimulatory activity on the Balb/c $^3$H-thymidine incorporation assay. The data in Table 4 show that the stimulatory activity in DP-B conditioned medium is unaffected by filtration on PD-10 columns. When 20 μg/ml cycloheximide is present continuously during the preparation of conditioned medium the stimulatory activity of conditioned medium is reduced by approximately 50%. Stimulatory activity similar to the control value (6.60) is obtained from conditioned medium to which cycloheximide (20 μg/ml) is added prior to sequential gel filtration and subsequent assay of the final void fraction. This indicates that cycloheximide is removed efficiently from conditioned medium and that DP-B cells have to be exposed to cycloheximide during the preparation of conditioned medium for the reduction in stimulatory activity to occur. These data provide evidence that the stimulatory activity present in DP-B conditioned medium is proteinaceous and is dependent on cellular protein synthesis.

Transformed Dermal Papilla Cell Line DP-B

Two lines of evidence indicate that the rat vibrissa dermal papilla cell line, DP-B, is a spontaneously transformed variant of primary dermal papilla cells. Firstly, it was detected as a rapidly proliferating variant at an early serial passage of a primary vibrissa dermal papilla cell culture and can be serially transferred indefinitely (greater than about 50 passages) whereas primary dermal papilla cell cultures undergo terminal senescence after about 10–15 passages. Secondly, the growth characteristics of DP-B cells confirm that they are better adapted to growth in Vitro than primary dermal papilla cells (FIG. 1 and Table 1). The DP-B cell line appears to have a reduced requirement for serum components when compared to primary dermal papilla cells (FIG. 1). The ability to grow in low serum is a characteristic of many virally transformed cell lines (Todaro, G. J., H. Green & B. D. Goldberg (1964) *Proc. Natl. Acad. Sci. USA*, 51, 66–73; Benjamin, T. L. (1974), *Methods in Cell Biology*, 8, 368–437); and in many instances this phenomenon is related to the secretion into the culture medium of mitogenic factors by the transformed cells (DeLarco, J. E. & G. J. Todaro (1978), *Proc. Natl. Acad. Sci. USA*, 75, 4001–4005; Ozanne, B., R. J. Fulton & P. L. Kaplan, (1980), *J. Cell. Physiol.*, 105, 163–180. The spontaneously transformed dermal papilla cell line releases stimulatory factor(s) into the culture medium. The mitogenic activity in DP-B conditioned medium was detected as a 2 to 3-fold stimulation in $^3$H-thymidine incorporated into TCA-precipitable material of Balb/c 3T3 cells (Table 2) and by the maintenance of cell proliferation (FIG. 2). This particular cell line is widely used to detect broad-purpose mitogenic activity because it has been shown to respond to a wide variety of mitogens (Armelin, H. A (1973), *Proc. Natl. Acad. Sci. USA*, 70, 2702–2706; Klagsbrun, M., R. Langer, R. Levenson, S. Smith & C. Lillehei (1977) *Exp Cell. Res.*, 105 99–108; Lieberman, M. A., P. Rothenburg, D. M. Raben & L. Glaser, (1980), *Biochem. Biophys. Res. Comm.*, 92, 696–702; Raines, E. W. & R. Ross (1982), *J. Biol. Chem.*, 257, 5154–5160). DP-B conditioned medium also stimulates DNA synthesis in primary culture of rat vibrissa and human hair follicle dermal papilla cells and equivalent skin fibroblasts (Table 2). The factor(s) that mediates the stimulation of DNA synthesis in both the permanent Balb/c 3T3 line and the primary cultures can be concentrated by ultrafiltration on membranes whose retention limit is 5,000 D (Table 3). The factor(s) is not concentrated by membranes whose retention limit is greater than about 15,000D. This indicates that the mitogenic active factor is likely to have a molecular weight less than about 15,000D or that the mitogenic active factor requires the presence of one or more cofactors of molecular weight less than about 15,000D.

Transformed dermal papilla cell line DP-B has been received by the PHLC Centre for Applied Microbiology & Research, European Collection of Animal Cell Cultures, Division of Biologies, Porton Down Salisbury, Wiltshire SP4 OJG, UK on Mar. 29, 1990. The deposited strain has been assigned accession number 90032810. The subject culture has been deposited under conditions that assure access to the culture will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that Applicants' granting of permission to the depository to distribute samples of the deposit does not constitute an express or implied license to practice the invention claimed in any patent issuing on the subject application or any other patent.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The presence of protease and cycloheximide-sensitive mitogenic factors in DP-B conditioned medium is consistent with the observation that DP-B cells act as effective feeder layers that support the proliferation of rat skin keratinocytes in vitro.

The production of mitogenic activities of broad specificity by a dermal papilla-derived cell line suggests a possible role for these factors in the regulation of keratinocyte proliferation during the hair cycle and also in the maintenance and regeneration of the dermal papilla cell population within hair folliclds.

TABLE 1

Growth Characteristics of Primary Rat Dermal Papilla (pRDP) Cell Culture and the DP-B Permanent Cell Line

| Cell Type | Mean Cell Number After 9 Days (+SE) ($\times 10^3$ per well) | Population Doubling Time[a] (Hours) |
|---|---|---|
| pRDP (10% FCS) | 55.4 ± 38.2 | 26.6 |
| pRDP (1% FCS) | 2.9 ± 1.5 | 120.2 |
| DP-B (10% FCS) | 772.8 ± 75.3 | 13.9 |
| DP-B (1% FCS) | 28.9 ± 0.61 | 36.0 |

[a]Population doubling times were obtained during the first 72 hour period of growth.

TABLE 2

$^3$H-Thymidine Incorporation Assay of DP-B Conditioned Medium

| Target Cells | Thymidine Incorporation (Mean ± SD) | (c.f. control = 1) |
|---|---|---|
| Balb/c 3T3 | 2.85 ± 0.99 (n = 22) | |
| Rat Skin Fibroblast | 2.34 ± 2.23 (n = 6) | |
| Rat Dermal Papilla | 1.91 ± 0.85 (n = 5) | |
| Human Skin Fibroblast | 1.82 ± 0.97 (n = 8) | |
| Human Dermal Papilla | 2.87 ± 0.76 (n = 6) | |

The target cells were treated with DP-B conditioned medium and assayed as described in Materials and Methods. In each case the data is shown as the ratio of the radioactivity (dpm/16 mm well) incorporated into TCA precipitable material after treatment with conditioned medium to that obtained after treatment of control cultures with additive-free DMEM.

"n" refers to the number of separate experiments performed.

TABLE 3

$^3$H-Thymidine Incorporation Assay of DP-B Conditioned Medium Samples Prepared by Membrane Ultrafiltration

| Sample | Thymidine Incorporation (c.f. control = 1)[a] | |
|---|---|---|
| | DMEM | DP-B Conditioned Medium |
| Before Ultrafiltration | 1.00 | 2.90 |
| Concentrates: | | |
| 20× | 1.10 | 13.63 |
| 10× | 1.23 | 11.13 |
| 5× | 1.40 | 6.32 |
| 2.5× | 1.45 | 4.09 |
| 1× | 1.43 | 2.44 |
| Filtrate[b] | 0.94 | 1.43 |

[a] In each case the data is shown as the ratio of the radioactivity (d.p.m./16 mm well) incorporated by Balb/c 3T3 cells into TCA-precipitable material after treatment with a test sample to that obtained after treatment with additive-free DMEM before ultrafiltration.
[b] Filtrates were obtained from DMEM and DP-B conditioned medium following 20-fold membrane concentration procedure.

TABLE 4

$^3$H-Thymidine Incorporation Assay of DP-B Conditioned Medium Prepared in Presence of Cycloheximide

| Sample Description | Thymidine Incorporation (d.p.m. ± S.E.) | Thymidine Incorporation (c.f. Control = 1) |
|---|---|---|
| Dulbecco's Medium Control | 30656 (±1981) | 1.00 |
| DP-B Conditioned Medium | 144742 (±9560) | 4.72 |
| PD10 DESALT COLUMN TREATED SAMPLES | | |
| DP-B Conditioned Medium | 202254 (±13515) | 6.60 |
| DP-B Conditioned Medium with added Cycloheximide (20 μg ml$^{-1}$) | 155857 (±6013) | 5.80 |
| DP-B Medium Conditioned in 20μ ml$^{-1}$ Cycloheximide | 80917 (±3977) | 2.64 |

We claim:

1. A composition suitable for topical application to mammalian skin or hair, comprising an amount of a cell-free supernatant from a culture of dermal papilla cells which is sufficient to increase hair growth in mammals, the dermal papilla cells having the characteristics of cell line 90032810, cell line 90032810 being a transformed cell line which can be serially transferred indefinitely, the supernatant comprising a proteinaceous hair growth factor possessing the ability to initiate DNA synthesis in a culture of serum starved 3T3 cells.

2. A composition according to claim 1 in which the supernatant comprises a proteinaceous hair growth promoter which is characterized by possessing the ability to initiate DNA synthesis in a culture of serum starved 3T3 cells.

3. A composition according to claim 2 in which the hair growth promoter has an apparent molecular weight of from about 5000D about 15,000D.

4. A composition according to claim 2 which comprises a cosmetically-acceptable vehicle in addition to the culture supernatant.

5. A composition according to claim 1 in which the supernatant comprises from about 5 ng/ml to about 200 ng/ml of one or more members of the IGF-family selected from the group consisting of insulin, IGF-I and IGF-II.

6. A composition according to claim 5 in which the IGF Family member is IGF-I.

7. A transformed dermal papilla cell line having the characteristics of cell line 90032810, cell line 90032810 being a transformed cell line which can be serially transferred indefinitely.

8. A composition suitable for topical application to mammalian skin or hair comprising:
  i) an amount of a hair growth promoter, or active fragments thereof, sufficient to increase hair growth in mammals, and
  ii) a cosmetically-acceptable vehicle,
the hair growth promoter having been obtained from a cell-free supernatant of cultured dermal papilla cells having the characteristics of cell line 90032810, cell line 90032810 being a transformed cell line which can be serially transferred indefinitely, the hair growth promoter being proteinaceous, and being further characterized by possessing the ability to initiate DNA synthesis in a culture of serum starved 3T3 cells.

9. A composition suitable for topical application to mammalian skin or hair comprising:
  i) an amount of hair growth promoter, or active fragments thereof, sufficient to increase hair growth in mammals, and
  ii) a cosmetically-acceptable vehicle,
the hair promoter having been obtained from a cell-free supernatant of cultured dermal papilla cells having the characteristics of cell line 90032810, cell line 90032810 being a transformed cell line which can be serially transferred indefinitely, following:
  a) inoculation of a nutrient medium with the dermal papilla cells,
  b) incubation at a temperature of from about 15° C. to about 45° C. for at least about 24 hours,
  c) separation of the supernatant liquor from the culture;
the hair growth factor so obtained being characterized by possessing the ability to at least double the synthesis of DNA in serum starved 3T3 cells as measured by uptake of tritiated thymidine.

10. A process for the preparation of a hair growth promoter, which comprises the steps of:
  i) inoculating a nutrient medium with dermal papilla cells having the characteristics of cell line 90032810, cell line 90032810 being a transformed cell line which can be serially transferred indefinitely;
  ii) incubating with the medium at a temperature of from about 14° C. to about 45° C.; and
  iii) separating the supernatant from the culture; and the concentrate so obtained containing a proteinaceous hair growth promoter which is characterized by possessing the ability to initiate DNA synthesis of serum-starved 3T3 cells.

11. The process of claim 10 which further comprises the step of concentrating the cell-free supernatant at least about 50 times.

12. A composition suitable for topical application to mammalian skin or hair, comprising an amount of a cell-free supernatant from a culture of cell line 90032810 which is sufficient to increase hair growth in mammals, cell line 90032810 being a transformed cell line which can be serially transferred indefinitely, the supernatant comprising a proteinaceous hair growth factor possessing the ability to initiate DNA synthesis in serum starved 3T3 cells.

* * * * *

UNITED STATES PATENT AND TRADEMARK OFFICE
CERTIFICATE OF CORRECTION

PATENT NO. : 5,091,173

DATED : February 25, 1992

INVENTOR(S) : Buultjens et al.

It is certified that error appears in the above-identified patent and that said Letters Patent is hereby corrected as shown below:

Column 2, line 9 "( )" should read --(•).

Column 6, line 15 "tryprinized" should read --trypsinized--.

Column 9, line 15 "in Vitro" should read --in vitro--.

Column 12, line 50 "$14°$" should read --$15°$--.

Signed and Sealed this

Eighteenth Day of May, 1993

Attest:

MICHAEL K. KIRK

Attesting Officer     Acting Commissioner of Patents and Trademarks